United States Patent [19]

Segre

[11] 3,932,635
[45] Jan. 13, 1976

[54] NOVEL CYCLIC PROGESTOGEN-INTERRUPTED ESTROGEN ORAL CONTRACEPTIVE REGIMENS

[75] Inventor: Eugene J. Segre, Los Altos, Calif.
[73] Assignee: Syntex Corporation, Panama, Panama
[22] Filed: May 5, 1972
[21] Appl. No.: 250,785

Related U.S. Application Data
[63] Continuation-in-part of Ser. No. 247,012, April 24, 1972.

[52] U.S. Cl. ............................................. 424/239
[51] Int. Cl.² ........................................ A61K 17/06
[58] Field of Search ................................... 424/239

[56] References Cited
UNITED STATES PATENTS

| | | | |
|---|---|---|---|
| 3,409,721 | 11/1968 | Applezweig | 424/239 |
| 3,591,688 | 7/1971 | Jones et al. | 424/239 |
| 3,624,203 | 11/1971 | Overbeek | 424/238 |
| 3,660,574 | 5/1972 | Berman | 424/238 |
| 3,755,573 | 8/1973 | Berman | 424/238 |

OTHER PUBLICATIONS

Haspels, A. A., Fortschritte Der Therapie 90(Suppl.):595–600, May 18, 1972, "Die Pille Danach"– "Experience of 1,000 Women with the Postcoital Administration of High Estrogen Doses".
Haspels, A. A., I.P.P.F. Medical Bull. 3:6–(1969), "The Morning After Pill–A Preliminary Report".
Morris, et al., Amer. J. Obstet. Gynec., 96:804–815, Nov. 15, 1966 "Compounds Interfering with Ovum Implantation and Development III the Role of Estrogens".
Ball, Canad. Med. Assn. JL.105: 240, Aug. 7, 1971, "The Morning–After Pill".
Rudel, Fed. Proc. 29:1228–1231, May, June 1971, Antifatility Effects of Low Dose Progestin.
Cox, J. Reprod. Fert. Suppl. 5, (1968:167–172, The pre–coital use of Mini–Dosage Progestogens.
Foss, J. Reprod. Fert. Suppl., 5(1968):145–154, Oral Contraception with Continuous Microdosage of Norgestrel.
Rudel et al., IBPT, Sect, 48 Vol. 2385–417, (1972), "Oral Contraceptives, Hamon Fertility Studies and Side Effects," Pergamon Press, N.Y. (1972).
Green Blatt Fertility & Sterility 18:207–211, (1967), One Pill a Month Contraceptive.
Coutinho et al., J. Reprod. Fert. 16:137–139, (1968), The Every Other Day Pill.
Lotvin et al., Obstet. Gynocol. 35:933–936, June 1970, Once A Month Oral Contraceptive Quinestrol and Quingestanol.
Claman, Amer. J. Obstet. Gynec.107:461–464, June 1970, A Trial of a One Dose a Month Oral Contraceptive.

Primary Examiner—Shep K. Rose
Attorney, Agent, or Firm—Joseph I. Hirsch; William B. Walker

[57] ABSTRACT

This invention relates to a method of fertility control by use of novel cyclic progestogen-interrupted estrogen oral contraceptive regimens. Considering the first day of menstrual flow as day one of a 28 day medication administration cycle, a combined formulation of estrogen and progestogen substances is administered on the 3rd, 4th, 5th or 6th day of the cycle and every second or third day thereafter through, and including, the 23rd, 24th, 25th, 26th, 27th or 28th day of the cycle, and a formulation having only a progestogen substance as the active component is administered on the 4th, 5th, 6th, or 7th day of the cycle and every day thereafter on which a combination formulation is not administered, through, and including, the 22nd, 23rd, 24th, 25th, 26th, 27th or 28th day of the cycle.

In a particular regimen, a combination of estrogen and progestogen is administered starting with the 5th day of the cycle and continuing every other day through the 25th day of the cycle, and starting with the 6th day of the cycle and continuing every other day through the 24th day of the cycle only progestogen is administered. The remaining seven days are dosage-free or the regimen is completed by use of placebos or other non-hormonal supplements.

Dispensing packages for holding unit dosage forms for oral ingestion of one unit dosage form daily in the appropriate sequence during a single cycle of medication administration are also described.

21 Claims, No Drawings

NOVEL CYCLIC PROGESTOGEN-INTERRUPTED ESTROGEN ORAL CONTRACEPTIVE REGIMENS

CROSS-REFERENCE TO RELATED APPLICATION

This application is a continuation-in-part application of application Ser. No. (247012) filed Apr. 24, 1972, entitled "Novel Oral Contraceptive Regimens and Packaged Unit Dosage Forms Thereof", and assigned to the assignee of the present invention.

BACKGROUND OF THE INVENTION

The present invention relates to a method of fertility control in the human female by adherence to a novel oral contraceptive regimen. The regimen includes the administration of a combination of an estrogen and a progestogen during certain days of the reproductive cycle, and the administration of only the progestogen on certain of the other days of the cycle.

Research and development in the area of human contraception or fertility control has heretofore concentrated almost exclusively on preventative methods, whether in the form of chemical or physical diversions of or barriers to sperm transport, e.g., vaginal creams and foams, condoms, diaphragms, and intrauterine devices, or in the form of chemically based oral contraceptive. The former methods have been largely supplanted by the use of oral contraceptives which have proven to be extremely effective in the prevention of conception. This effectiveness, however, necessarily requires the administration of the oral contraceptive tablets over approximately 21 days of each reproductive cycle. During the remaining 7 days of the 28 day cycle, no hormone-containing tablets are given and it is during this period, if the reproductive cycle is accurately regulated, that normal menstrual flow takes place.

The most common form of oral contraception is based upon the daily administration of a combination of estrogen and progestogen substances for about 21 successive days, starting generally on the 5th day of the menstrual cycle. After the 21 day period, there follows a 7 day period during which neither the estrogen or progestogen substances are taken. If the reproductive cycle of the female has been properly regulated, the normal and characteristic menstrual flow is supposed to, and generally does, occur within the 7 day period.

A second method which has been developed is the "sequential" system wherein from the 5th through about the 19th day of the cycle only an estrogen is given. A different tablet containing both estrogen and progestogen substances is given for the 5 days from the 20th to the 24th day of the cycle. This regimen more closely approximates the time-related secretion by the female body of its own reproductive cycle-controlling hormones. As with the combined treatment, there are no hormonal substances given during the 7 days following the 24th day. If the reproductive cycle has been properly regulated, the normal menstrual flow will, and generally does, occur within the 7 day period.

Although oral contraceptives have proven to be extremely effective in controlling fertility, the administration of oral contraceptive formulations, like other potent drugs, has some side effects. Since the oral contraceptives maintain a pseudopregnancy condition, the most commonly occuring side effects are similar to the common symptoms observed during pregnancy. Such side effects may be attributable to the potent estrogenic and progestogenic agents administered during the course of the regimen. Accordingly, it is of continuing interest to those in this field to develop new oral contraceptive regimens which control fertility, yet do so with lower dosages of estrogen and/or progestogen agents, minimized side effects, or do so in an improved manner.

Thus, Coutinho and deSouza, J. Reprod. Fert.16,1-37–139, (1968) suggest the administration of a combined tablet containing estrogen and progestogen every other day starting on the 5th day of the menstrual cycle and ending on the 23rd day of the cycle. On intervening days between the 5th and the 23rd days of the cycle, no tablets or placebos are administered. Although it was concluded that the contraceptive effectiveness of such a regimen is unaltered by extending the interval of administration to alternate days (as opposed to administration on 21 consecutive days), the reported data also shows that this was achieved with some sacrifice in cycle regulation and duration of menstrual flow. Specifically, regulation of the reproductive cycle to give menstrual flow upon termination of medication (i.e., so called "withdrawal bleeding") was only effective in slightly over 50% of the cycles recorded. This loss of cycle regulation can, in turn, expose the patient to the possibility of conception during an "unprotected" period (i.e., where no active medication is being taken) which does not coincide with actual menstrual flow. Additionally, the complete absence of menstrual flow (i.e. amenorrhoea) increased significantly as did those instances where the duration of menstrual flow was undesirably long (i.e., greater than 8 days).

BRIEF SUMMARY OF THE INVENTION

The method of controlling fertility, according to the present invention, comprises administering to the human female during certain days of the reproductive cycle a combination of estrogen and progestogen, and administering during certain other days of the reproductive cycle only a progestogen. This is considered an "interrupted treatment," as distinguished from the "combined" and "sequential" treatments described above.

In the broadest aspects, the present invention relates to methods for controlling fertility in women wherein the first day of menstrual flow prior to the initiation of the administration of oral contraceptive medication is considered as day 1 of a medication administration cycle. On the 3rd, 4th, 5th, or 6th day of the cycle and every second or third day thereafter through, and including, the 23rd, 24th, 25th, 26th, 27th, or 28th day of the cycle, there is administered a combination formulation having both esterogen and progestogen substances. On the 4th, 5th, 6th or 7th day of the cycle and every day thereafter on which a combination formulation is not administered, through, and including, the 22nd, 23rd, 24th, 25th, 26th, 27th, or 28th day of the cycle, a formulation having only a progestogen substance as the active component is administered. On the remaining days of the cycle, active medication may be given in alternating or interrupted form, if desired. Generally, however, the remaining days are dosage-free or the regimen is completed by use of placebos or non-hormonal supplements. If the reproductive cycle of the female has been regulated by such a regimen, menstrual flow (i.e., "withdrawal bleeding") will, and usually does, occur shortly after discontinuance of the administration of active medication.

According to a particular regimen, the first day of menstrual flow is considered to be the first day of the initial medication administration cycle. On the 5th day and every other day through, and including, the 25th day of the cycle, there is administered a combined formulation having both estrogen and progestogen substances. On the 6th day of the cycle and every other day through, and including, the 24th day of the cycle, there is administered a formulation having only a progestogen as the active component. For the remaining 7 days of the 28 day cycle (i.e., days 26–28 and days 1–4) no estrogenic or progestogenic substances are taken. Optionally, during this 7 day period, plecebos with or without non-hormonal supplements can be administered to provide a continuous program of oral contraception administration over successive cycles. If the reproductive cycle of the female has been regulated by the above-described regimen, menstrual flow will, and usually does, occur shortly after the 25th day (i.e., after discontinuance of the administration of the estrogenic/progestogenic substances).

The progestogen component of the oral contraceptive regimen is generally administered daily in an amount from about 0.03 mg. to about 10.0 mg., generally from about 0.3 mg. to about 1.0 mg., throughout period of therapy. The actual amount of progestogen utilized in a daily unit dosage form will depend upon the particular progestogen utilized and its relative potency or activity. For example, a smaller quantity of a more potent progestogen will be required to achieve the same results as a larger quantity of a less potent progestogen. The presently preferred progestogen is norethindrone (ie, $17\alpha$-ethynyl-$17\beta$-hydroxy-estr-4-en-3-one), as described in U.S. Pat. No. 2,744,122. Other progestogens include chlormadinone-acetate (6-chloro-17-hydroxy-pregna-4,6-diene-3,20-dione acetate), norethynodrel ($17\alpha$-ethynyl-17-hydroxy-estr-5(10)-en-3-one), norgestrel ($13\beta$-ethyl-$17\alpha$-ethynyl-$17\beta$-hydroxy-gon-4-en-3-one), medroxy-progesterone acetate ($17\alpha$-acetoxy-$6\alpha$-methyl-pregn-4-ene-3,20-dione), megestrol acetate ($17\alpha$-acetoxy-6-methyl-pregna-4,6-diene-3,20-dione), lynestrenol ($17\alpha$-ethynyl-$17\beta$-hydroxy-estr-4-ene), quingestrone (3-cyclopentyloxy-pregna-3,5-diene-20-one), norethindrone acetate ($17\beta$-acetoxy-$17\alpha$-ethynyl-estr-4-en-3-one), ethynodiol acetate ($3\beta,17\beta$-diacetoxy-$17\alpha$-ethynyl-estr-4-ene), dimethisterone [$17\beta$-hydroxy-$6\alpha$-methyl-17-(1-propynyl)-androst-4-en-3-one], other orally active progestogens, and the like.

On those days that the estrogen component of the oral contraceptive regimen is administered it is administered in an amount from about 0.01 mg. to about 2.0 mg., generally from about 0.03 mg. to about 0.1 mg. As with the progestogen substance, the actual amount of estrogen substance utilized in a unit dosage form will depend upon the particular estrogen utilized and its relative potency or activity. Estrogen administration is preferably in a combined unit dosage form along with the progestogen; however, the estrogen can be administered in separate unit dosage form if so desired. The presently preferred estrogen is ethinyl estradiol (ie, $17\alpha$-ethynyl-$3,17\beta$-dihydroxy-estra-1,3,5(10)-triene). Other estrogens include mestranol ($17\alpha$-ethynyl-$17\beta$-hydroxy-3-methoxy-estra-1,3,5(10)-triene). estradiol ($3,17\beta$-dihydroxy-estra-1,3,5(10)-triene), estriol($3,-16\alpha,17\beta$-trihydroxy-estra-1,3,5(10)-triene), estrone (3-hydroxy-estra-1,3,5(10)-triene-17-one), diethylstilbestrol, quinestradiol (3-cyclopentyloxy-$16\alpha,17\beta$-dihydroxy-estra-1,3,5-(10)-triene, and other orally active estrogens, and the like.

Each of the estrogenic and progestogenic substances utilized in this regimen performs the same function or functions that it would if given, for example, in accordance with the "combined" treatment referred to above. However, it has been found that oral contraceptives, administered according to the regimen herein described, control fertility although administered at a substantially reduced dosage level (as compared, for example, to oral contraceptive unit dosage forms presently commercially marketed by the assignee of the present invention) while retaining satisfactory control over reproductive cycle length and duration of menstrual flow.

The process of the present invention is conventionally practiced by administration of the oral contraceptive formulations during a 28 day cycle, as described above. The formulations are prepared from the estrogenic and progestogenic agents to provide the combined estrogen/progestogen formulation and individual progestogen formulation, both as described above. The active component or components is, or are, as the case may be, in admixture with a pharmaceutically acceptable non-toxic carrier. Thus, the formulations can be appropriately compounded in any pharmaceutically acceptable non-toxic form and packaged in any manner suitable for proper delivery and use. For example, the formulations can take the form of tablets, capsules, and/or pills containing in addition to the active component or components, a number of inert materials including diluents, binders, lubricants, and/or other additives designed to improve its physical characteristics. See Remington's *Pharamaceutical Sciences*, Mack Publishing Company, Easton, Penn., 14th Edition, 1970, especially Chapter 87. As used herein, "unit dosage form" refers to any suitable manner, such as the use of tablets, capsules, and/or pills, etc., by which the formulations of the present invention, including, optionally, placebos, are made available to the user thereof for daily ingestion according to the regimen herein described.

Dispensing packages according to this invention, and particularly useful herein, include those which accommodate the required formulation representing daily unit dosage forms in a contiguous, sequential arrangement which, if properly used according to the instructions packaged therewith, cause the proper formulation to be taken at the appropriate time during the reproductive cycle. For example, such a dispensing package may comprise individual blister pods for the storage in each of a single unit dosage form. At the appropriate time during the reproductive cycle, the unit dosage form is manually dispensed therefrom through a frangible retaining layer. Storage of other unit dosage forms is not affected by such dispensing. Appropriate notations can be placed on the dispensing package, if desired, to guide or instruct the user thereof in the proper use of the oral contraceptive herein described. For example, day of the week, day of the cycle, miscellaneous instructions, etc., may be provided, if so desired.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

EXAMPLE I 5,000 pink tablets having the following composition are prepared:

| | | |
|---|---|---|
| norethindrone | 0.5 | mg. |
| ethynyl estradiol | 0.06 | mg. |
| lactose (USP) | 55.2 | mg. |
| corn starch | 19.2 | mg. |
| polyvinylpyrrolidone | 4.8 | mg. |
| magnesium stearate | 0.24 | mg. |
| F D & C red No. 2 dye | 0.007 | mg. |

In the following procedure, appropriate quantities of each component are utilized to give the desired number of tablets, each tablet having the composition listed above.

The norethindrone and ethynyl estradiol are disolved in ethanol which is heated slightly. The dye is dissolved in water and both solutions are mixed. The lactose, corn starch, and polyvinylpyrrolidone are mixed and passed through a No.40 mesh screen. The mixed solution of norethindrone and ethynyl estradiol is added to the powder mixture of lactose, corn starch, and polyvinylpyrrolidone, and granulated through a No.12 mesh screen. This mixture is dried at 40°–45°C and then passed through a No.20 mesh screen. The magnesium stearate is passed through a No. 60 mesh screen, added to the grandulated powder and mixed for three minutes. The tablets are prepared from this granulated power by compressing portions thereof using a 6mm. diameter flat face beveled edge punch.

EXAMPLE II 5,000 uncolored tablets having the following composition are prepared:

| | | |
|---|---|---|
| norethindrone | 0.5 | mg. |
| lactose (USP) | 55.26 | mg. |
| corn starch | 19.20 | mg. |
| polyvinylpyrrolidone | 4.8 | mg. |
| magnesium stearate | 0.24 | mg. |

The method of preparing the tablets of this Example is the same as is given above in Example I, except the ethynyl estradiol and F D and C red No.2 dye are omitted.

In the preceding formulations, the polyvinylpyrrolidone can vary between 4–6%, by weight, of the total weight of the tablet, the corn starch can vary between 19–25%, by weight, of the total weight of the tablet, the magnesium stearate can vary between 0.2–0.5%, by weight, of the total weight of the tablet, the coloring dye can be added as required, and the lactose is added in sufficient amount to bring individual tablets to their desired weight. Generally the lactose represents about 50–75%, by weight, of the total tablet weight.

Placebo tablets can be prepared from polyvinylpyrrolidone, corn starch, magnesium stearate, an appropriate coloring dye, and lactose in amounts, for example, as specified in the preceding paragraph.

Eleven tablets having the composition as shown in Example I, 10 tablets having the composition as shown in Example II, and 7 placebos are placed in a dispensing package. Considering the first day of menstrual flow as day one, placebos are placed in the first four individual storage pods. The eleven tablets corresponding to the composition of Example I are placed, one each, in the storage pods corresponding to the fifth day and every other day thereafter through, and including, the 25th day. The 10 tablets corresponding to the composition of Example II are placed, one each, in the storage pods corresponding to the 6th day and every other day thereafter through, and including, the 24th day. The remaining 3 placebos are placed, one each, in the 3 remaining individual storage pods corresponding to days 26–28. Appropriate notations are made on the dispensing package instructing the user thereof to take the first placebo tablet on the first day of menstrual flow. The dispensing package also includes additional instructions directing the user thereof to take the remaining tablets, at one tablet per day, in the specified sequence during the remaining days of the 28 day cycle.

In an alternate dispensing package, the 7 placebo tablets are omitted. Appropriate instructions are placed on the dispensing package directing the user thereof to consider the 1st day of menstrual flow as the day 1 of the cycle, to commence the taking of the tablets in the sequence as shown on day 5 of the cycle, and to continue taking such tablets at one tablet per day until all of the tablets have been ingested. The dispensing package also includes additional instructions directing the user thereof to wait 7 days prior to starting the next regimen with a new dispensing package of tablets.

In either case, using either the 21 or 28 tablet-containing dispensing package, the administration of active medication will begin for each succeeding cycle on the same day of the week as administration of active medication began during the first cycle. For as long as the patient is maintained on this regimen by the physician this 28 day cycle will be adhered to, regardless of whether menstrual flow has taken place or not during the "unprotected" period.

EXAMPLE III

Eighty-one women with proven fertility and exposed to occurrence of pregnancy, but who are not using any other means of contraceptive or fertility control, are administered the oral contraceptives of the present invention according to the regimen described in Examples I and II above.

The results obtained in this clinical study are tabulated below in Table I. As used in Table I, "menstrual flow interval" refers to the number of days from the first day of menstrual flow for one cycle until the first day of menstrual flow for the next succeeding cycle; the "duration of menstrual flow" means the actual number of days of menstrual flow. Three patients involved in the clinical studies tabulated in Table I were on the program for too short a period of time to obtain meaningful data with regard to the interval of menstrual flow. Thus, only 78 patients are listed under that category in Table I. However, one such patient did have a bleeding episode during the time on the program and, thus, is included in the data tabulated in Table I under duration of menstrual flow.

TABLE I

| MENSTRUAL FLOW INTERVAL (DAYS) | PATIENTS | | CYCLES | |
|---|---|---|---|---|
| | No. | % | No. | % |
| <25 | 14 | 17.9 | 98 | 18.2 |
| 25–32 | 49 | 62.9 | 375 | 69.9 |
| >32 | 13 | 16.7 | 52 | 9.7 |
| >60 | 2 | 2.6 | 12 | 2.2 |
| | 78 | | 537 | |

DURATION OF MENSTRUAL FLOW

TABLE I-continued

| MENSTRUAL FLOW INTERVAL (DAYS) | PATIENTS No. | % | CYCLES No. | % |
|---|---|---|---|---|
| < 3 | 12 | 15.2 | 74 | 12.2 |
| 3–8 | 67 | 84.8 | 531 | 87.3 |
| > 8 | — | — | 3 | 0.5 |
| | 79 | | 608 | |

No pregnancies occurred; accordingly, this represents a pregnancy rate of 0.0 per 100 women years. As used herein, "pregnancy rate" is the number of pregnancies × 1,200 divided by the product of the number of patients observed × the months of exposure.

With regard to Table I above, the menstrual flow interval represented by 25–32 days is commonly referred to as "withdrawal bleeding". That is, it refers to the occurrence of menstrual flow shortly after the administration of active medication is terminated (i.e., during the "unprotected" period during which the placebos are taken or no tablets are taken). As can be seen from the data presented in Table I, in a substantial majority (ie, approximately 70%) of the cycles tabulated to date, withdrawal bleeding has occurred as desired. In addition, the incidence of amenorrheic cycles (as categorized by a menstrual flow interval greater than 60 days) is relatively modest and, in any event, is a substantial improvement over the results reported by Coutinho et al, supra. With regard to duration of menstrual flow, the duration of a substantial majority (ie, approximately 87%) of menstrual flow episodes recorded fall within the desired 3–8 day range. Thus, these results reflect that the regimen described herein is effective in preventing conception, controlling the duration of flow, and regulating the length of the reproductive cycle, as evidence by the high incidence of "withdrawal bleeding" where the time of actual menstrual flow is desirably synchronized with the "unprotected" period. As indicated above, this is achieved with a substantial reduction in the amount of active components administered to the patient.

EXAMPLES IV and V

The compositions of Examples I and II are repeated except 0.5 mg. of norethindrone acetate is substituted for the 0.5 mg. norethindrone in each instance.

EXAMPLES VI and VII

The compositions of Examples I and II are repeated except 6.0 mg. of dimethisterone is substituted for the 0.5 mg. norethindrone in each instance.

EXAMPLES VIII and IX

The compositions of Examples I and II are repeated except 0.5 mg. of norethynodrel is substituted for the 0.5 mg. norethindrone in each instance.

EXAMPLES X and XI

The compositions of Examples I and II are repeated except 0.5 mg. of ethynodiol acetate is substituted for the 0.5 mg. norethindrone in each instance.

EXAMPLES XII and XIII

The compositions of Examples I and II are repeated except 0.25 mg. of norgestrel is substituted for the 0.5 mg. norethindrone in each instance.

EXAMPLES XIV and XV

The compositions of Examples I and II are repeated except 5.0 mg. of medoxyprogesterone acetate is substituted for the 0.5 mg. norethindrone in each instance.

EXAMPLES XVI and XVII

The compositions of Examples I and II are repeated except 0.5 mg. of chlormadione acetate is substituted for the 0.5 mg. norethindrone in each instance.

The present invention has been particularly described above with reference to not only an effective regimen, but one that conforms to an accepted mode of administration of oral contraceptives to a large number of women of varying backgrounds, intelligence, inclinations, etc. That is, the regimen has been based upon a medication administration cycle requiring 21 days on medication and 7 days off medication, whereby in each succeeding cycle the administration of active medication begins on the same day of the week as in the first or preceding cycle. However, from a theoretical point of view without regard to the convenience of use aspect, the present invention can be modified in certain particulars which are considered to be within the broad concepts of this invention.

For example, a combined formulation having both estrogen and progestogen substances can be administered on the 3rd day of the medication administration cycle and a progestogen formulation administered on the 4th day of the cycle. This is followed by the 21 days of medication administration as described above, whereby active medication is administered on 23 days of a 28 day cycle.

Alternatively, administration of the interrupted regimen can be as given above with the exception that no medication is given on the 25th day. In this aspect of the invention, administration of active medication ends on the 24th day with the administration only of the progestogen substance.

In a further aspect of the invention, once again considering the first day of menstrual flow prior to the initiation of administration of medication as day one, the administration of active medication can begin on the 3rd, 4th, 5th, or 6th day of the cycle with the administration of a combined estrogen and progestogen formulation. The combined formulation, however, is only administered every third day. On intervening days, only a progestogen substance is administered.

Thus, in the broadest aspects of the invention, combined estrogen and progestogen formulations are administered on the 3rd, 4th, 5th, or 6th, day of the cycle and every second or third day thereafter through, and including, the 23rd, 24th, 25th, 26th, 27th, or 28th day of the cycle. On the 4th, 5th, 6th, or 7th day of the cycle and every day thereafter on which a combination formulation is not administered, through, and including, the 22nd, 23rd, 24th, 25th, 26th, 27th, 28th day of the cycle, formulation having only a progestogen substance as the active component is administered. On the remaining days of the cycle, the regimen may be completed by additional active medication or placebos, etc., as indicated above. Generally, however, active medication will be given for only a period of 20–23 days.

Dispensing packages accommodating the novel oral contrceptive regimen of this invention, with or without placebos, are also considered a part of the present invention. As indicated above, such packages include instructions directing the user thereof to take a single unit dosage form daily in the desired sequence, whereby the proper formulation is ingested on the proper day during the medication administration cycle. Suitable packages include those shown by Applezweig U.S. Pat. No. 3,409,721, and those oral contraceptive packages presently marketed by the assignee of the present invention. A further package has one row of combined estrogen/progestogen unit dosage forms, and a second row of unit dosage forms having only progestogen as the active component. One unit dosage form is taken from one row and the next unit dosage form is taken from the other row, and so on, alternating back and forth. Placebos may be added at the beginning and/or end of each row, if so desired.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:

1. A cyclic progestogen-interrupted estrogen method of controlling fertility in a fertile woman wherein the first day of menstrual flow is considered as day 1 of a 28 day cycle, said method comprising orally administering to said woman beginning on one of the 3rd to 6th days of said cycle and every second or third day thereafter a combination oral dosage unit formulation having about 0.01 mg. to about 2.0 mg. of an estrogen and about 0.03 mg. to about 10.0 mg. of a progestogen, and orally administering to said woman beginning on one of the 4th to 7th days of said cycle and every day thereafter on which a combination formulation is not administered an oral dosage unit formulation having only a progestogen in an amount of about 0.03 mg. to about 10.0 mg. as the active contraceptive component, said formulations being administered for a period of 20 to 23 consecutive days during said 28 day cycle, said amounts of said estrogen and progestogen being effective to control the fertility of said woman.

2. The method of claim 1 further including administering placebos on those days of said cycle on which a progestogen substance is not administered, said placebos containing neither estrogen nor progestogen substances.

3. The method of claim 1 further including repeating said 28 day cycle of medication administration at least one further time, the first day of the next succeeding cycle following directly after the 28th day of the preceding cycle.

4. The method of claim 1 wherein said combination of estrogen and progestogen substances is administered every third day.

5. The method of claim 1 wherein said progestogen is selected from the group consisting of norethindrone, norethindrone acetate, chlormadione acetate, norethynodrel, norgestrel, medroxyprogesterone acetate, megestrol acetate, lynestrenol, quingestrone, ethynodiol acetate, and dimethisterone.

6. The method of claim 1 wherein said combination formulation contains about 0.03 mg. to about 0.1 mg. of said estrogen substance and about 0.3 mg. to about 1.0 mg. of said progestogen substance, and said formulation having only a progestogen substance as the active component contains about 0.3 mg. to about 1.0 mg. of said progestogen substance.

7. The method of claim 1 wherein said combination of estrogen and progestogen substances is administered every second day.

8. The method of claim 7 wherein said estrogen is 17α-ethynyl-3,17β-dihydroxy-estra-1,3,5(10)-triene.

9. The method of claim 7 wherein said progestogen is 17α-ethynyl-3,17β-hydroxy-estr-4-en-3-one.

10. The method of claim 7 wherein said combination formulation comprises about 0.5 mg. 17α-ethynyl-17β-hydroxy-estr-4-en-3-one and about 0.06 mg. 17α-ethynyl-3,17β-dihydroxy-estra-1,3,5(10)-triene, and said formulation having only a progestogen substance as the active component contains about 0.5 mg. 17α-ethynyl-17β-hydroxy-estr-4-en-3-one.

11. A cyclic progestogen-interrupted estrogen method of controlling fertility in a fertile woman wherein the first day of menstrual flow is considered as day 1 of a 28 day cycle, said method comprising orally administering to said woman on the 5th day of said cycle and every other day through, and including, the 25th day of said cycle a combination oral unit dosage formulation having about 0.01 mg. to about 2.0 mg. of an estrogen and about 0.03 mg. to about 10.0 mg. of a progestogen, and orally administering to said woman on the 6th day and every other day through, and including, the 24th day of said cycle a formulation having only a progestogen in an amount of about 0.03 mg. to about 10.0 mg. as the active contraceptive component, said amounts of said estrogen and progestogen being effective to control the fertility of said woman.

12. The method of claim 11 further including administering placebos on the 7 consecutive days following the 25th day of said cycle, said placebos containing neither estrogen nor progestogen substances.

13. The method of claim 11 wherein no estrogenic or progestogenic medication is administered during days 1–4 and 26–28 of said cycle; said method further including repeating said 28 day cycle of medication administration at least one further time, the first day of the next succeeding cycle following directly after the 28th day of the preceding cycle.

14. The method of claim 11 wherein said progestogen is 17α-ethynyl-17β-hydroxy-estr-4-en-3-one.

15. The method of claim 11 wherein said estrogen is 17α-ethynyl-3,17β-dihydroxy-estra-1,3,5(10)-triene.

16. The method of claim 11 wherein about 0.06 mg. of 17α-ethynyl-3,17β-dihydroxy-estra-1,3,5(10)-triene is administered as said estrogen.

17. The method of claim 11 wherein said combination formulation comprises a combination of 17α-ethynyl-17β-hydroxy estr-4-en-3-one and 17α-ethynyl-17β-dihydroxy-estra-1,3,5(10)-triene.

18. The method of claim 11 wherein said combination formulation comprises about 0.5 mg. 17α-ethynyl-17βhydroxy-estr-4-en-3-one and about 0.06 mg. 17α-ethynyl-3,17βdihydroxy-estra-1,3,5(10)-triene, and said formulation having only a progestogen substance as the active component contains about 0.5 mg. 17α-ethynyl-17β-hydroxy-estr-4-en-3-one.

19. The method of claim 11 wherein about 0.5 mg. 17α-ethynyl-17β-hydroxy-estr-4-en-3-one is administered every other day from the sixth day of said cycle through, and including, the 24th day of said cycle.

20. The method of claim 11 wherein said progestogen is selected from the group consisting of norethindrone, norethindrone acetate, chlormadione acetate, norethynodrel, norgestrel, medroxyprogesterone acetate, megestrol acetate, lynestrenol, quingestrone, ethynodiol acetate, and dimethisterone.

21. The method of claim 11 wherein said combination formulation contains about 0.03 mg. to about 0.1 mg. of said estrogen substance and about 0.3 mg. to about 1.0 mg. of said progestogen substance, and said formulation having only a progestogen substance as the active component contains about 0.3 mg. to about 1.0 mg. of said progestogen substance.

* * * * *

UNITED STATES PATENT OFFICE
CERTIFICATE OF CORRECTION

Patent No. 3,932,635                    Dated January 13, 1976

Inventor(s) EUGENE J. SEGRE

It is certified that error appears in the above-identified patent and that said Letters Patent are hereby corrected as shown below:

Column 2, lines 8-9, "1-37" should read -- 137 --. Column 3, line 64, "-triene)." should read -- -triene), --. Column 5, line 30 "power" should read -- powder --. Column 6, lines 67-68, cancel "DURATION OF MENSTRUAL FLOW". Column 7, lines 4-6, cancel "MENSTRUAL FLOW INTERVAL (DAYS)    ". Column 7, line 7, "(DAYS)" should read -- DURATION OF MENSTRUAL FLOW (DAYS) --. Column 9, line 4, "contrceptive" should read -- contraceptive --. Claim 9, line 2, "3,17β" should read -- 17β --. Claim 17, line 3, "17β" should read -- 3,17β --. Claim 18, line 3, "17βhydroxy" should read -- 17β-hydroxy --. Claim 18, line 4, "3,17βdihydroxy" should read -- 3,17β-dihydroxy --.

Signed and Sealed this

Twenty-fourth Day of August 1976

[SEAL]

Attest:

RUTH C. MASON
Attesting Officer

C. MARSHALL DANN
Commissioner of Patents and Trademarks